(12) United States Patent
Williams et al.

(10) Patent No.: US 10,369,245 B2
(45) Date of Patent: Aug. 6, 2019

(54) SYSTEM FOR TREATING EMISSIONS FROM A VEHICLE

(71) Applicant: Safety Step, LLC, Roanoke, VA (US)

(72) Inventors: James Philip Williams, Monroe, GA (US); Mike Ray Williams, Auburn, GA (US)

(73) Assignee: Safety Step, LLC, Roanoke, VA (US)

( * ) Notice: Subject to any disclaimer, the term of this patent is extended or adjusted under 35 U.S.C. 154(b) by 0 days.

(21) Appl. No.: 16/025,312

(22) Filed: Jul. 2, 2018

(65) Prior Publication Data

US 2019/0070331 A1    Mar. 7, 2019

Related U.S. Application Data

(60) Provisional application No. 62/605,900, filed on Sep. 1, 2017.

(51) Int. Cl.
| | |
|---|---|
| *A61L 9/04* | (2006.01) |
| *A61L 9/12* | (2006.01) |
| *A61L 9/20* | (2006.01) |
| *C02F 1/32* | (2006.01) |
| *C02F 1/78* | (2006.01) |
| *B01D 53/34* | (2006.01) |
| *B01D 53/38* | (2006.01) |

(52) U.S. Cl.
CPC .............. *A61L 9/12* (2013.01); *A61L 9/046* (2013.01); *A61L 9/20* (2013.01); *B01D 53/34* (2013.01); *C02F 1/325* (2013.01); *C02F 1/78* (2013.01); *A61L 2209/12* (2013.01); *A61L 2209/14* (2013.01); *A61L 2209/212* (2013.01); *B01D 53/38* (2013.01); *B01D 2251/104* (2013.01); *B01D 2257/90* (2013.01); *B01D 2257/91* (2013.01); *B01D 2259/4566* (2013.01)

(58) Field of Classification Search
CPC ........ A61L 9/12; A61L 9/046; A61L 2209/12; A61L 2209/212
USPC ............. 250/428, 430, 431, 432 R, 434, 435
See application file for complete search history.

(56) References Cited

U.S. PATENT DOCUMENTS

| | | | |
|---|---|---|---|
| 4,752,401 | A | 6/1988 | Bodenstein |
| 5,256,379 | A | 10/1993 | DeLoach |
| 5,935,431 | A | 8/1999 | Korin |
| 5,972,196 | A | 10/1999 | Murphy et al. |
| 6,096,219 | A | 8/2000 | Green et al. |
| 6,117,324 | A | 9/2000 | Green et al. |
| 6,129,849 | A | 10/2000 | Yoshikawa et al. |
| 6,156,192 | A | 12/2000 | Rummler |
| 6,528,021 | B1 | 3/2003 | Williams |
| 7,468,135 | B2 | 12/2008 | Holt |

*Primary Examiner* — Nicole M Ippolito
*Assistant Examiner* — Hanway Chang
(74) *Attorney, Agent, or Firm* — Steve LeBlanc, LLC

(57) ABSTRACT

A system for treating emissions from a vehicle includes an ozone generator, a first holding tank, and an exhaust vent. The first holding tank is downstream from the ozone generator and defines a volume for liquid waste beneath a void space. The exhaust vent is downstream from the first holding tank and outside of the vehicle. A supply conduit connects the ozone generator to the void space of the first holding tank. An exhaust conduit connects the void space of the first holding tank to the exhaust vent. The ozone generator, supply conduit, void space of the first holding tank, exhaust conduit, and exhaust vent establish a thermal driving head from the ozone generator through the void space of the first holding tank to the exhaust vent.

14 Claims, 6 Drawing Sheets

SYSTEM FOR TREATING EMISSIONS FROM A VEHICLE

RELATED APPLICATIONS

The present application claims priority to previously-filed non-provisional application filed Sep. 1, 2017, assigned application Ser. No. 62/605,900, and titled "METHOD AND APPARATUS FOR NEUTRALIZING ODORS AND KILLING SURFACE AND AIRBORNE PATHOGENS IN RECREATIONAL VEHICLE AND MARINE WASTE HOLDING TANKS," which is incorporated by reference in its entirety for all purposes. Any disclaimer that may have occurred during prosecution of the above-referenced application is hereby expressly rescinded.

FIELD OF THE INVENTION

The present invention generally involves a system for treating bacterial, viral, and/or odor emissions from a vehicle. In particular embodiments of the present invention, the system may reduce or neutralize odors and/or airborne pathogens from a holding tank in the vehicle.

BACKGROUND OF THE INVENTION

Many vehicles such as boats, campers, trains, and aircraft include kitchens, bathrooms, and other facilities that generate various forms of liquid waste. Environmental concerns and movement of the vehicles generally prohibit or prevent discharging the liquid waste directly to the environment during operation of the vehicles. As a result, the vehicles often include one or more holding tanks that collect and store the liquid waste for subsequent disposal.

The liquid waste may be stored in the holding tanks for hours, days, or longer, and during this time, the liquid waste generates a wide variety of bacteria and other pathogens that emit undesirable odors and create the potential to spread disease to the surrounding environment. As a result, each holding tank often includes an exhaust vent outside of the vehicle that directs undesirable odors and other contaminants away from passengers inside the vehicle. While effective at preventing or reducing the spread of odors or contaminants inside the vehicle, the exhaust vent nonetheless allows the odors and contaminants to spread to areas outside the vehicle. For example, undesirable odors are typically present in the immediate vicinity of the exhaust vent outside the vehicle. In addition, particulates and other contaminants entrained in the exhaust tends to collect in higher concentrations on surfaces near the exhaust vent, increasing the risk of disease to people in the vicinity of the exhaust vent.

Various attempts have been made to neutralize odors and/or airborne pathogens from holding tanks. For example, pressurized systems or pumps may be used to inject chemicals or perfumes into the holding tanks to react with the liquid waste, but the chemicals and perfumes generally produce hazardous waste that requires additional disposal efforts, and the pressurized systems or pumps can be costly additions that require additional maintenance. Furthermore, pipes and fittings installed in the interior of a waste holding tank can obstruct or retard the flow of body waste, toilet paper and other objects when draining said tank in violation of plumbing code. Therefore, the need exists for a more cost-effective system to treat bacterial, viral, and other contaminants generated in holding tanks in vehicles to reduce or eliminate undesirable odors and contaminants in the vicinity of the vehicle.

BRIEF DESCRIPTION OF THE INVENTION

Aspects and advantages of the invention are set forth below in the following description, or may be obvious from the description, or may be learned through practice of the invention.

One embodiment of the present invention is a system for treating emissions from a vehicle. The system includes an ozone generator, a first holding tank, and an exhaust vent. The first holding tank is downstream from the ozone generator and defines a volume for liquid waste beneath a void space. The exhaust vent is downstream from the first holding tank and outside of the vehicle. A supply conduit connects the ozone generator to the void space of the first holding tank. An exhaust conduit connects the void space of the first holding tank to the exhaust vent. The ozone generator, supply conduit, void space of the first holding tank, exhaust conduit, and exhaust vent establish a thermal driving head from the ozone generator through the void space of the first holding tank to the exhaust vent.

In an alternate embodiment of the present invention, a system for treating emissions from a vehicle includes a first holding tank that defines a volume for liquid waste beneath a void space. An ozone generator is upstream from the first holding tank and in fluid communication with the void space of the first holding tank. An exhaust vent is downstream from the first holding tank and in fluid communication with the void space of the first holding tank. The ozone generator, void space of the first holding tank, and exhaust vent establish a thermal driving head from the ozone generator through the void space of the first holding tank to the exhaust vent.

In yet another embodiment of the present invention, a system for treating emissions from a vehicle includes a chamber, an axial flow path through the chamber, and an ultraviolet lamp in the axial flow path through the chamber. A first holding tank downstream from the chamber defines a volume for liquid waste beneath a void space. An exhaust vent downstream from the first holding tank is in fluid communication with the void space of the first holding tank. The ultraviolet lamp, void space of the first holding tank, and exhaust vent establish a thermal driving head from the chamber through the void space of the first holding tank to the exhaust vent.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
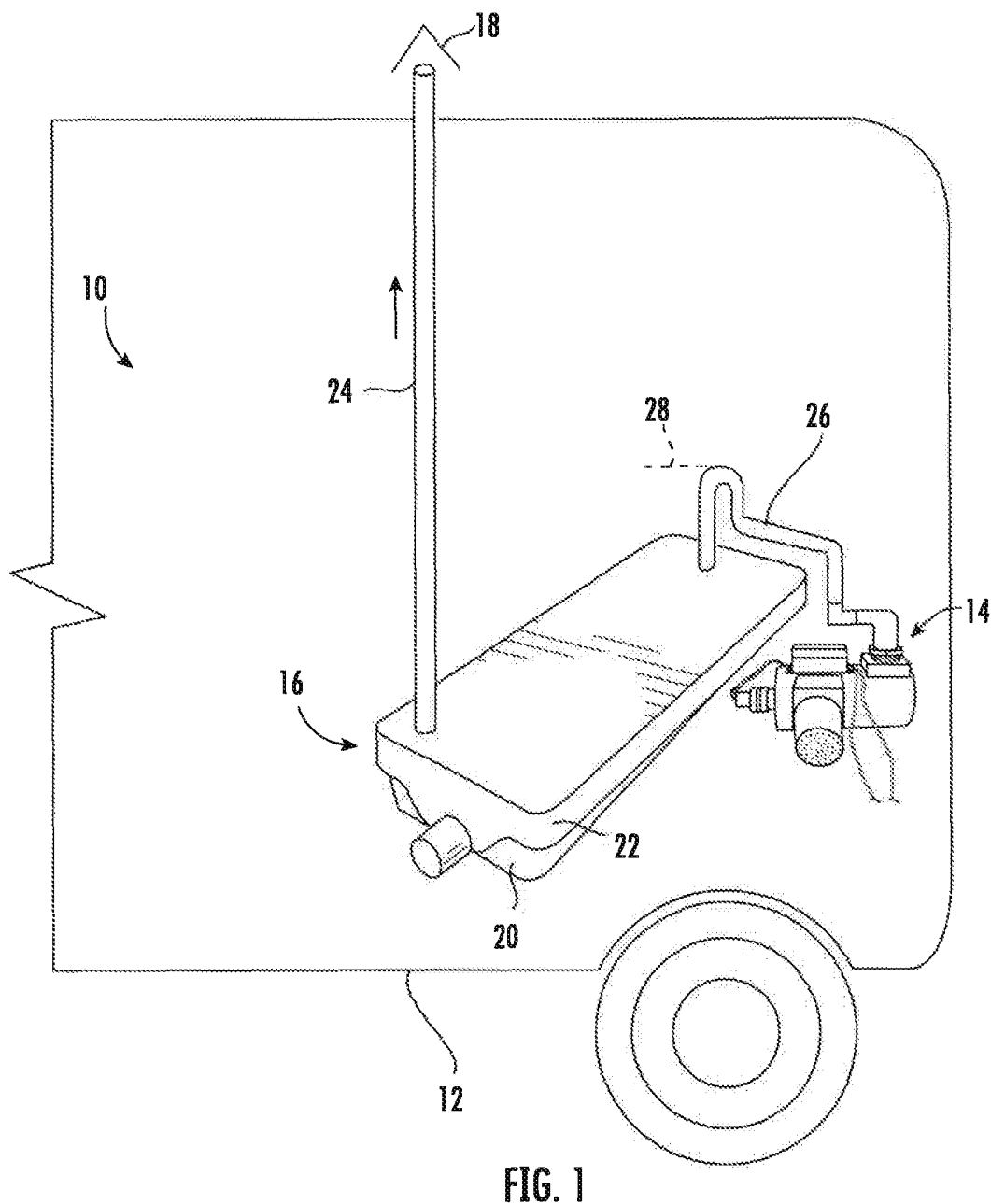
FIG. 1 is a perspective view of a system for treating emissions according to one embodiment of the present invention incorporated into a recreational vehicle.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Embodiments of the present invention provide a system 10 for treating emissions from a vehicle 12. As used herein, "vehicle" means anything used for transporting people or goods, such as a car, bus, recreational vehicle, boat, ship, or plane. The reference to vehicle in the preamble and body of the claims is for contextual purposes only and is not intended to be a limitation of any claim. As used herein, the terms "first," "second," and "third" may be used interchangeably to distinguish one component from another and are not intended to signify location or importance of the individual components. As used herein, the terms "upstream" and "downstream" refer to the relative location of components in a fluid pathway. For example, component A is upstream of component B if a fluid flows from component A to component B. Conversely, component B is downstream of component A if component B receives a fluid flow from component A. As used herein, the term "axial" refers to a direction of flow through an object; the term "radial" refers to a direction extending away from the center of an object or normal to the "axial" direction, and the term "circumferential" refers to a direction extending around the circumference or perimeter of an object.

Figure 2:
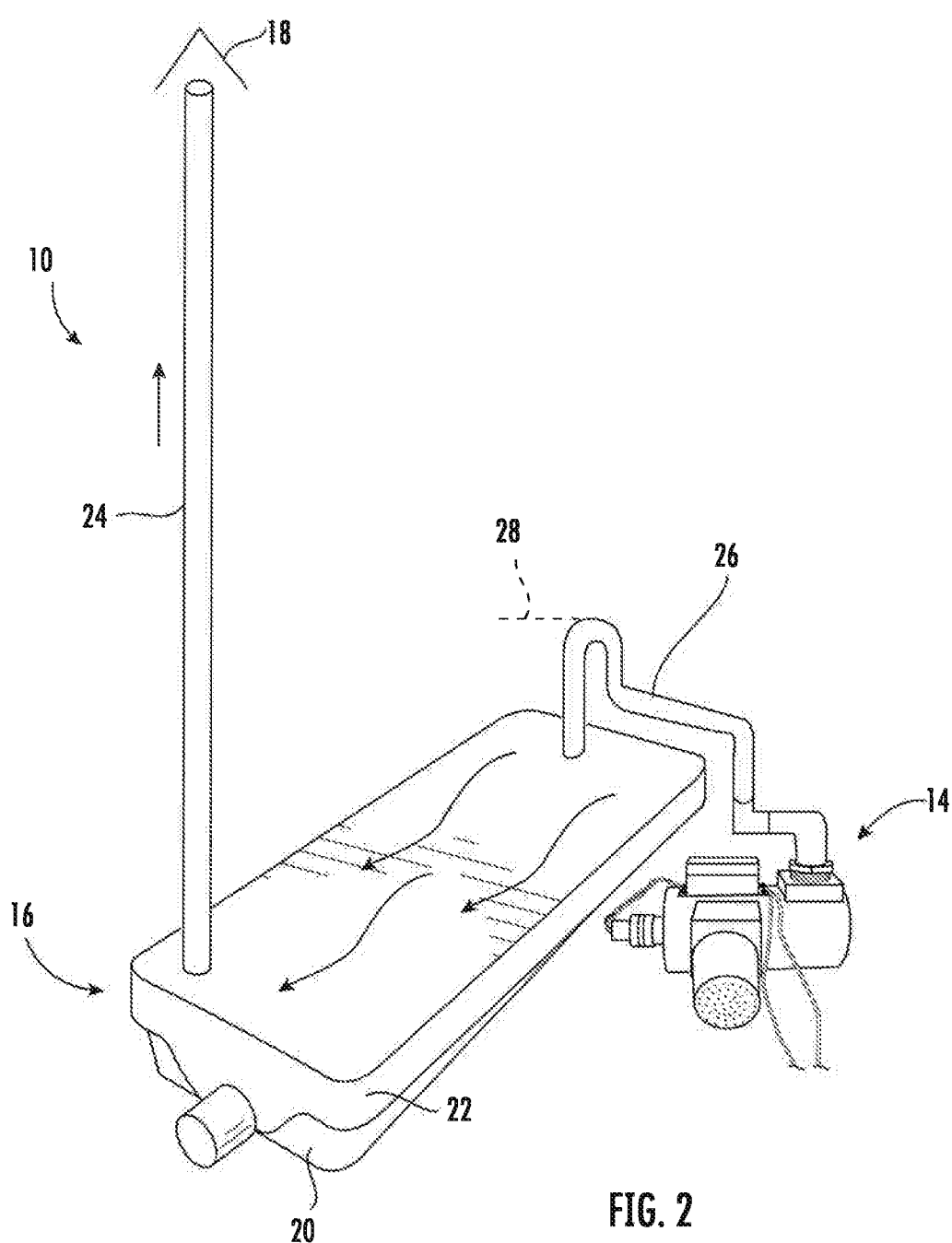
FIG. 2 is a simplified diagram of the system for treating emissions shown in FIG. 1.

FIG. 1 provides a perspective view of the system 10 for treating emissions according to one embodiment of the present invention incorporated into a recreational vehicle 12, and FIG. 2 provides a simplified diagram of the system 10 for treating emissions shown in FIG. 1. As shown in FIGS. 1 and 2, the system 10 generally includes an ozone generator 14, a first holding tank 16, and an exhaust vent 18. The ozone generator 14 produces a supply of ozone which is a known disinfectant and oxidizer that oxidizes and breaks down both organic and inorganic waste. A suitable ozone generator within the scope of the present invention will be described in more detail with respect to FIGS. 3 and 4.

The first holding tank 16 is a conventional tank present in many vehicles to receive and store various forms of liquid waste from kitchens, bathrooms, showers, and other facilities associated with the vehicle 12. As shown most clearly in FIG. 2, the first holding tank 16 defines a volume for liquid waste 20 beneath a void space 22. The liquid waste may include water, sewage, food products, and other solids drained from the kitchens, bathrooms, showers, or other facilities associated with the vehicle 12 that generate liquid waste for subsequent disposal. The void space 22 is simply the empty portion of the first holding tank 16 above the volume of liquid waste 20.

An exhaust conduit 24 may connect the void space 22 of the first holding tank 16 to the exhaust vent 18 to provide fluid communication from the void space 22 to the exhaust vent 18. In this manner, the exhaust conduit 24 and exhaust vent 18 allow the release of vapors produced in the first holding tank 16 to prevent any appreciable pressure build-up inside the first holding tank 16. In particular embodiments, the exhaust vent 18 may be located outside of the vehicle 12 to prevent released emissions from entering the passenger compartment of the vehicle 12, although the location of the exhaust vent 18 is not a limitation of the present invention unless specifically recited in the claims.

A supply conduit 26 may connect the ozone generator 14 to the void space 22 of the first holding tank 16. In this manner, the supply conduit 26 provides fluid communication from the ozone generator 14 downstream to the void space 22 of the first holding tank 16. In particular embodiments, the supply conduit 26 may have an elevation 28 above the first holding tank 16 to prevent inadvertent siphoning of liquid waste from the first holding tank 16 to the ozone generator 14.

Figure 3:
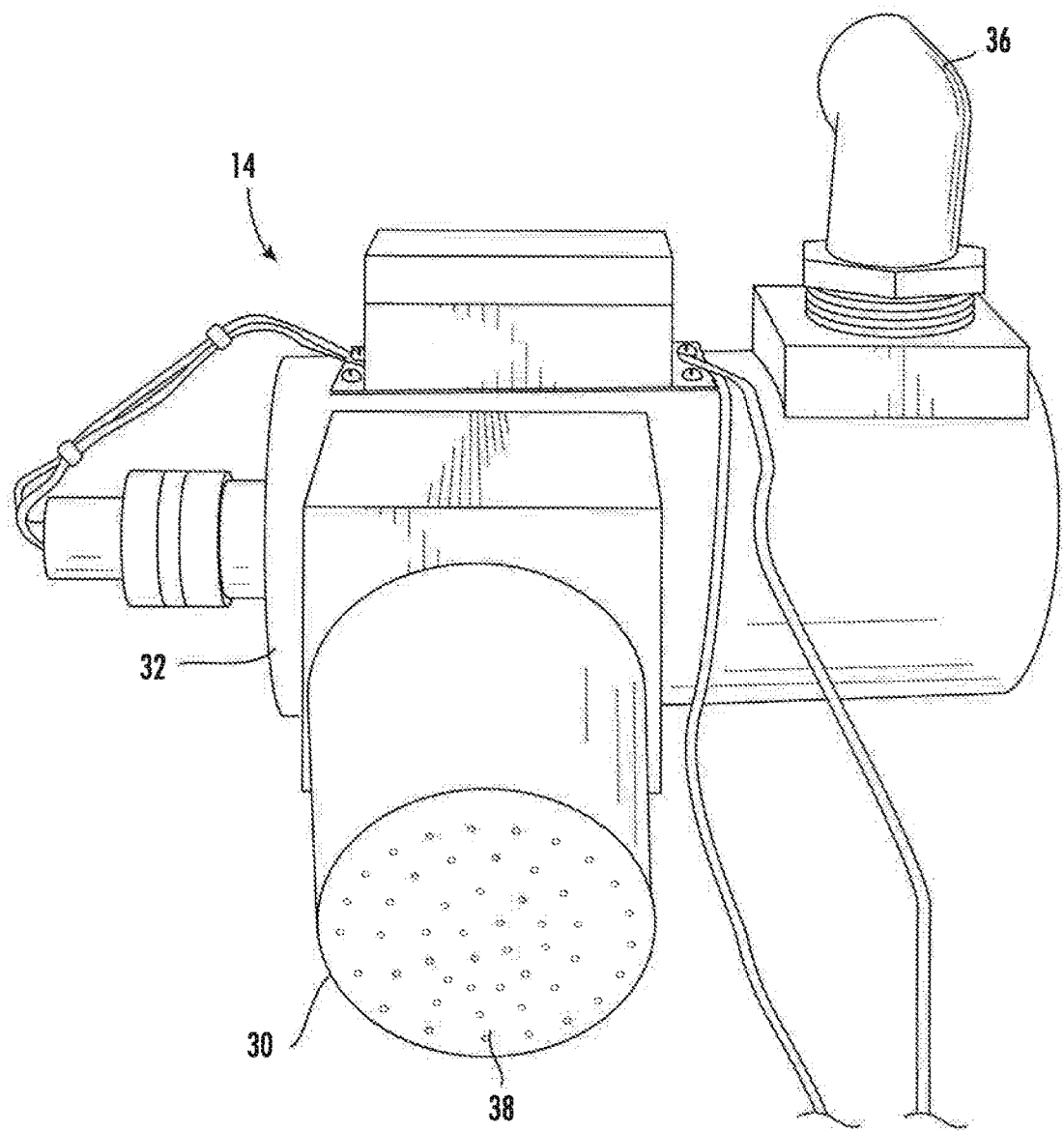
FIG. 3 is a perspective view of a representative ozone generator shown in FIG. 2.
Figure 4:
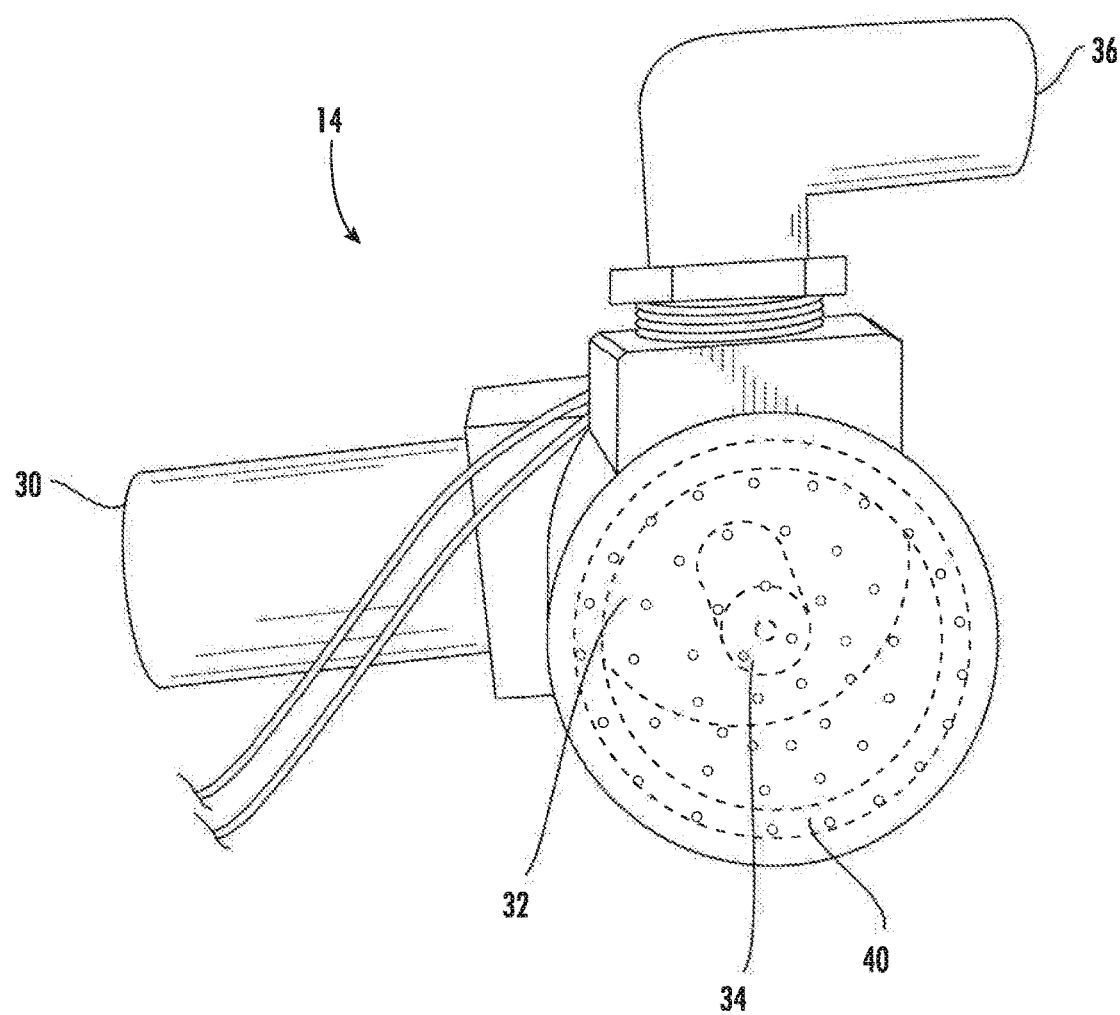
FIG. 4 is an axial perspective view of the ozone generator shown in FIG. 3.

FIG. 3 provides a perspective view of a representative ozone generator 14 shown in FIG. 2, and FIG. 4 provides an axial perspective view of the ozone generator shown in FIG. 3. As shown in FIGS. 3 and 4, the ozone generator 14 may include an inlet 30, a chamber 32 downstream from the inlet 30, an ultraviolet lamp 34 inside the chamber 32, and an outlet 36 downstream from the chamber 32. The inlet 30 allows ambient air to flow into the ozone generator 14 and may include a screen or other filter 38 to prevent the introduction of foreign material into the chamber 32. As shown most clearly in FIG. 4, with an end cap 40 of the chamber shown in phantom, the chamber 32 houses the ultraviolet lamp 34 and provides an axial flow path through the chamber 32 to allow ambient air to flow around and in proximity to the ultraviolet lamp 34.

The ultraviolet lamp 34 may generate light having a wavelength of approximately 185-254 nm, although the particular wavelength of the ultraviolet lamp 34 is not a limitation of the present invention unless recited in the claims. The ultraviolet lamp 34 heats the ambient air and converts diatomic oxygen in the ambient air flowing around and in proximity to the ultraviolet light 34 to tri-oxide or ozone. The ozone entrained in the ambient air then flows out of the chamber 32 and through the outlet 36 which is connected to the supply conduit 26 shown in FIGS. 1 and 2. In particular embodiments, the outlet 36 may be translucent to allow light from the ultraviolet lamp 34 to pass through the outlet 36. In this manner, light from the ultraviolet lamp 34 may be visually observed outside of the chamber 32 to readily indicate the operational status of the ultraviolet lamp 34 without opening the chamber 32.

Returning to FIG. 2, arrows illustrate the flow of ambient air and ozone through the system 10. As shown by the arrows in FIG. 2, ambient air flows into the ozone generator 14 where the ultraviolet lamp 34 generates ozone. The ozone entrained in the ambient air flow then flows downstream through the supply conduit 26 to the void space 22 in the first holding tank 16. Once in the void space 22, the ozone blankets any liquid waste in the first holding tank 16 to neutralize odors and reduce or eliminate surface and air-borne pathogens. The ozone entrained in the ambient air then exits the first holding tank 16 through the exhaust conduit 24 and exhaust vent 18.

Temperature differences in the system 10 create a thermal driving head to produce the ambient air flow shown in FIG. 2. Specifically, ambient air in the exhaust vent 18 and exhaust conduit 24 is typically heated during the day to create a chimney effect that produces a natural thermal updraft from the first holding tank 16. This naturally created thermal driving head in turn draws ambient air into the ozone generator 14, through the supply conduit 26, and into the void space 22 of the first holding tank 16. At night, when the chimney effect is less pronounced, heat generated by the ultraviolet lamp 34 produces a sufficient thermal driving heat to provide a continuous flow of ozone entrained in the ambient air through the supply conduit 26 and into the void space 22. As a result, the ozone generator 14, supply conduit 26, void space 22, exhaust conduit 24, and/or exhaust vent 18 combine to establish a sufficient thermal driving head to produce the desired flow of ozone from the ozone generator 14, through the void space 22, and out of the exhaust vent 18.

Figure 5:
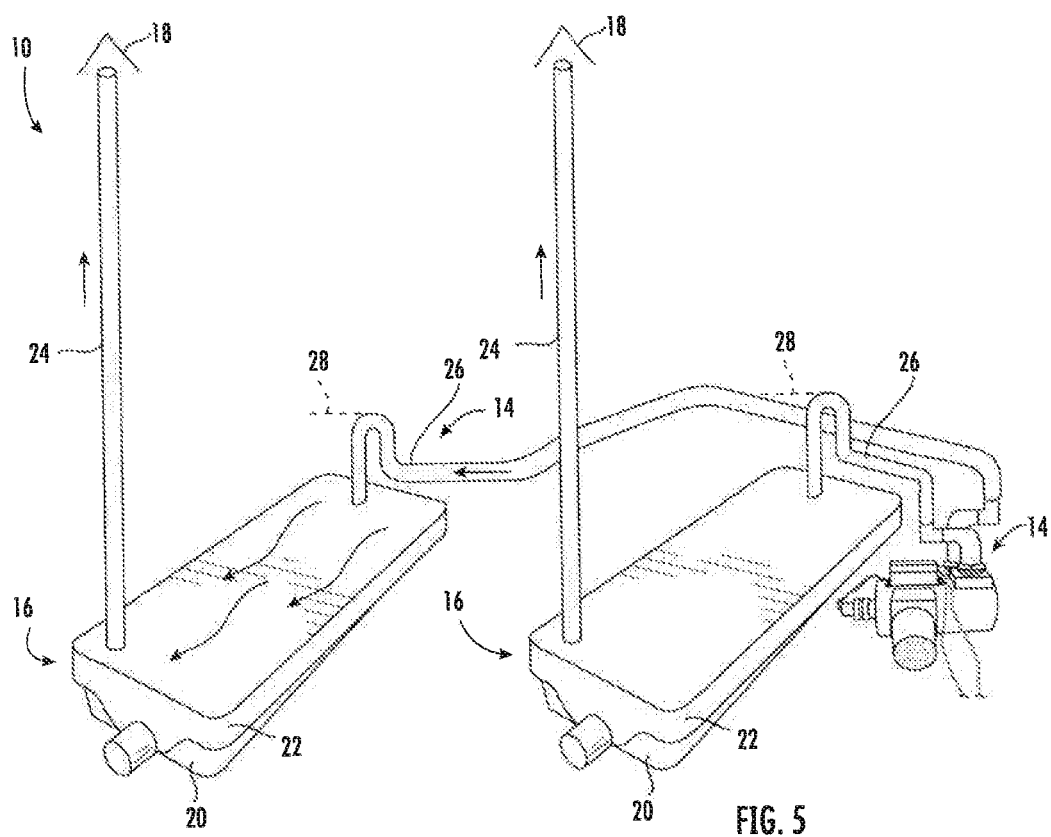
FIG. 5 is a simplified diagram of a system for treating emissions according to an alternate embodiment of the present invention.
Figure 6:
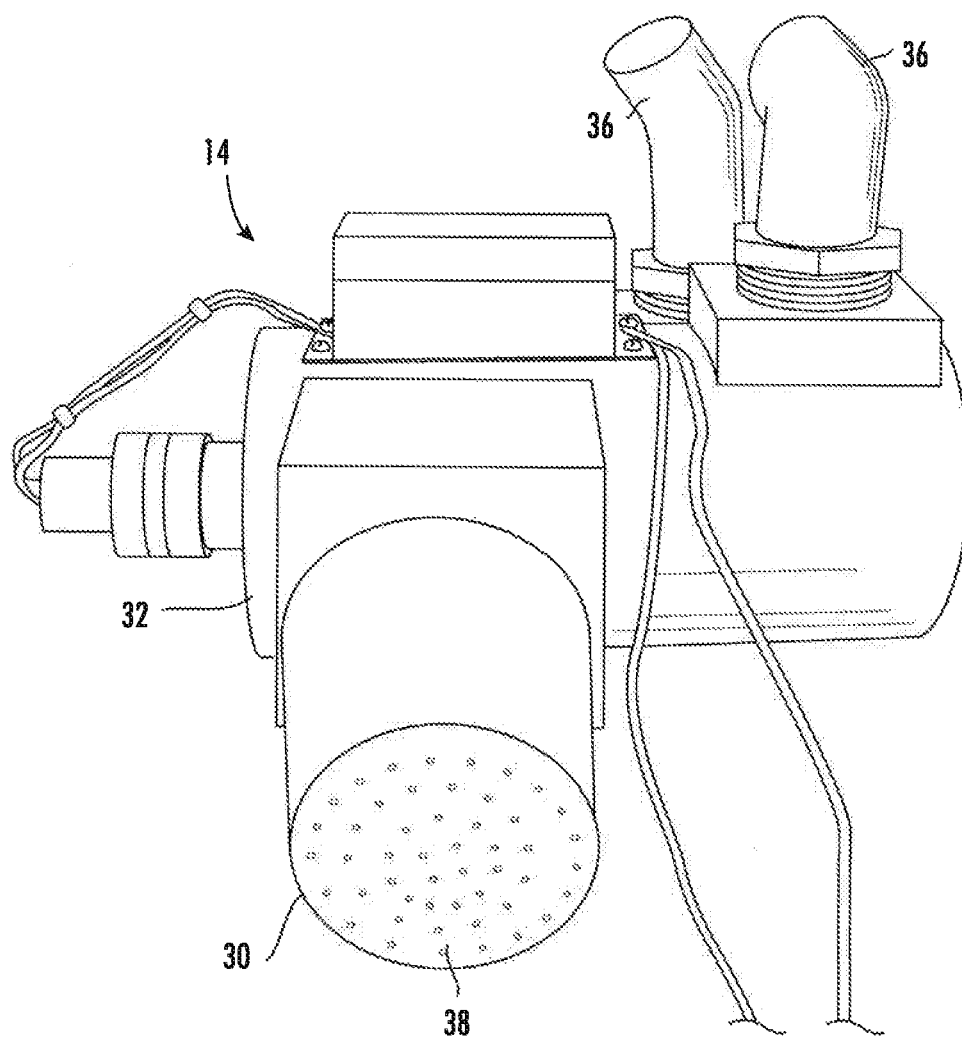
FIG. 6 is a perspective view of a representative ozone generator shown in FIG. 5.

FIG. 5 provides a simplified diagram of a system 10 for treating emissions according to an alternate embodiment of the present invention, and FIG. 6 provides a perspective view of the ozone generator 14 shown in FIG. 5. As shown in FIGS. 5 and 6, the system 10 again includes the ozone generator 14, first holding tank 16, exhaust vent 18, exhaust conduit 24, and supply conduit 26 as previously described and illustrated with respect to FIGS. 1-4. In this particular embodiment, the system 10 further includes a second holding tank 42 downstream from the ozone generator 14. The presence of two holding tanks 16, 42 allows liquid waste to be segregated according to its source to facilitate proper disposal according to the content of the liquid waste. For example, first holding tank 16 may be a "gray water" tank that receives liquid waste from gray water sources such as a kitchen or shower, and the second holding tank 42 may be a "black water" tank that receives liquid waste from a bathroom.

As shown in FIG. 6, the ozone generator 14 again includes the inlet 30, chamber 32, and ultraviolet lamp 34 (not visible) as previously described and illustrated with respect to FIGS. 3 and 4. In this particular embodiment, the ozone generator 14 includes two outlets 36, with each outlet 36 providing fluid communication for the ozone entrained in the ambient air to flow into the respective holding tanks 16, 42. Alternately, one of ordinary skill in the art will readily appreciate that the two outlets 36 may simply be a single outlet 36 with separate branches to each holding tank 16, 42. In this manner, the single ozone generator 14 may provide sufficient ozone flow to multiple holding tanks.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A system for treating emissions from a vehicle, comprising:
    an ozone generator;
    a first holding tank downstream from said ozone generator wherein said first holding tank defines a volume for liquid waste beneath a void space;
    an exhaust vent downstream from said first holding tank and outside of the vehicle;
    a supply conduit that connects said ozone generator to said void space of said first holding tank;
    an exhaust conduit that connects said void space of said first holding tank to said exhaust vent;
    wherein said ozone generator, said supply conduit, said void space of said first holding tank, said exhaust conduit, and said exhaust vent establish a thermal driving head from said ozone generator through said void space of said first holding tank to said exhaust vent.

2. The system as in claim 1, wherein said ozone generator comprises an inlet, a chamber downstream from said inlet, an ultraviolet lamp inside said chamber, and an outlet downstream from said chamber connected to said supply conduit.

3. The system as in claim 2, wherein said outlet downstream from said chamber is translucent.

4. The system as in claim 1, further comprising a second holding tank downstream from said ozone generator.

5. The system as in claim 1, wherein said supply conduit has an elevation above said first holding tank.

6. A system for treating emissions from a vehicle, comprising:
    a first holding tank wherein said first holding tank defines a volume for liquid waste beneath a void space;
    an ozone generator upstream from said first holding tank and in fluid communication with said void space of said first holding tank;
    an exhaust vent downstream from said first holding tank wherein said exhaust vent is in fluid communication with said void space of said first holding tank;
    wherein said ozone generator, said void space of said first holding tank, and said exhaust vent establish a thermal driving head from said ozone generator through said void space of said first holding tank to said exhaust vent.

7. The system as in claim 6, wherein said ozone generator comprises an inlet, a chamber downstream from said inlet, an ultraviolet lamp inside said chamber, and an outlet downstream from said chamber in fluid communication with said void space of said first holding tank.

8. The system as in claim 7, wherein said outlet downstream from said chamber is translucent.

9. The system as in claim 6, further comprising a second holding tank downstream from said ozone generator.

10. The system as in claim 6, further comprising a supply conduit that provides fluid communication between said ozone generator and said void space of said first holding tank, wherein said supply conduit has an elevation above said first holding tank.

11. A system for treating emissions from a vehicle, comprising:
    a chamber;
    an axial flow path through said chamber;
    an ultraviolet lamp in said axial flow path through said chamber;
    a first holding tank downstream from said chamber wherein said first holding tank defines a volume for liquid waste beneath a void space;
    an exhaust vent downstream from said first holding tank wherein said exhaust vent is in fluid communication with said void space of said first holding tank;

wherein said ultraviolet lamp, said void space of said first holding tank, and said exhaust vent establish a thermal driving head from said chamber through said void space of said first holding tank to said exhaust vent.

12. The system as in claim 11, wherein said chamber comprises a translucent outlet in fluid communication with said void space of said first holding tank.

13. The system as in claim 11, further comprising a second holding tank downstream from said chamber.

14. The system as in claim 11, further comprising a supply conduit that provides fluid communication between said chamber and said void space of said first holding tank, wherein said supply conduit has an elevation above said first holding tank.

* * * * *